United States Patent
Sarkadi et al.

(10) Patent No.: US 6,391,656 B2
(45) Date of Patent: May 21, 2002

(54) ASSAY AND REAGENT KIT FOR EVALUATION OF MULTI-DRUG RESISTANCE IN CELLS

(75) Inventors: Balász Sarkadi; László Homolya; Zsolt Holló, all of Budapest (HU)

(73) Assignee: SOLVO Biotechnology, Szeged (HU)

( * ) Notice: Subject to any disclaimer, the term of this patent is extended or adjusted under 35 U.S.C. 154(b) by 0 days.

(21) Appl. No.: 09/840,791

(22) Filed: Apr. 23, 2001

Related U.S. Application Data (62) Division of application No. 09/203,553, filed on Dec. 1, 1998, now Pat. No. 6,277,655, which is a continuation-in-part of application No. 08/928,528, filed on Sep. 12, 1997, now Pat. No. 5,872,014, which is a continuation of application No. 08/322,702, filed on Oct. 13, 1994, now abandoned.

Foreign Application Priority Data

Aug. 31, 1994 (HU) .......................................... P94-02511

(51) Int. Cl.⁷ ..................... G01N 33/536; G01N 33/533
(52) U.S. Cl. ................ 436/536; 435/6; 435/7; 435/7.1; 435/7.21; 435/29; 435/34; 435/968; 435/975; 435/5; 435/188; 435/184; 435/810; 435/4; 436/536; 436/546; 436/800; 436/808
(58) Field of Search .................... 436/536, 546, 436/800, 808; 435/975, 6, 29, 34, 968, 7, 5, 184, 188, 810, 7.21; 424/8, 12

(56) References Cited

U.S. PATENT DOCUMENTS

| | | | |
|---|---|---|---|
| 4,281,061 A | * | 7/1981 | Zuk et al. ................... 435/7 |
| 5,314,805 A | * | 5/1994 | Haugland et al. ........... 435/29 |
| 5,872,014 A | * | 2/1999 | Sarkadi et al. ............. 436/536 |

OTHER PUBLICATIONS

Homolya et al., "Fluorescent cellular indicators are Extruded by the Multidrug resistance Protein", The Journal of Biological Chemistry, vol. 268, No. 29, Oct. 15, 1993, pp. 21493–21496.*

Hollo et al., "Calcein accumulation as a fluorometric functional assay of the multidrug transporter", Biochimica et Biophysica Acta 1191 (1994) pp. 384–388.*

Liminga et al., "Microfluorometric Evaluation of calcein Acetoxymethyl ester as a probe for p–glycoprotein–mediated resistance . . . ", Experimental Cell Research, vol. 212, pp. 291–296, 1994.*

(List continued on next page.)

Primary Examiner—Long V. Le
Assistant Examiner—Lisa V Cook
(74) Attorney, Agent, or Firm—Kolisch, Hartwell, Dickinson, McCormack & Heuser, P.C.

(57) ABSTRACT

Disclosed herein are methods and reagent kits for the quantitative in vitro determination of the functional determination of multi-drug resistance in cells, as well as for the clinical screening of potential modulators of multi-drug resistant transport activity in cells. The method of the invention is based on the measurement of the accumulation rate of free calcein within the cells of the specimen (advantageously by fluorescence measurement), after exposing the cells in vitro to a cell permeable form of calcein that is a good substrate for MDR proteins present in the sample. The cell permeable form of calcein is converted within the cell by intracellular enzymes to free calcein. Comparison of free calcein accumulation in the presence and absence of a potential inhibitor of transport activity permits the rapid screening of such inhibitors. Additionally, evaluation of free calcein accumulation rates in the presence of inhibitors of all MDR transport in comparison with calcein accumulation rates in the presence of selective inhibitors of MDR transport permits the evaluation of the functional type of MDR being exhibited.

10 Claims, 6 Drawing Sheets

OTHER PUBLICATIONS

Kessel et al., Characterization of Multidrug resistance by Fluorescent Dyes, Cancer Research 51, pp. 4665–4670, Sep. 1991.*

Neyfakh, "Use of Fluorescent dyes as molecular probes for the study of multidrug resistance," Experimntal Cell Research, vol. 174, 1988, pp. 168–176.*

* cited by examiner

ASSAY AND REAGENT KIT FOR EVALUATION OF MULTI-DRUG RESISTANCE IN CELLS

This application is a division of application Ser. No. 09/203,553, filed Dec. 1, 1998, now U.S. Pat. No. 6,277,655, which is itself a continuation-in-part of application Ser. No. 08/928,528, filed Sep. 12, 1997, now U.S. Pat. No. 5,872, 014, which is itself a continuation of application Ser. No. 08/322,702, filed Oct. 13, 1994, now abandoned, which claimed the priority of Hungarian application P94-02511, filed Aug. 31, 1994, which are each incorporated by reference.

FIELD OF THE INVENTION

The present invention is directed to methods of screening test substances for their effect on multi-drug resistance in cells, and of characterizing the type and degree of multi-drug resistance exhibited by cells. The present invention utilizes a quantitative in vitro diagnostic assay method for determining the activity and concentration of transport proteins that cause multi-drug resistance in tumors (MDR proteins). The invention further relates to reagent kits for performing said assay method.

BACKGROUND OF THE INVENTION

The efficiency of chemotherapy of tumors is seriously affected or hindered by the onset of the so called multi-drug resistance that, with respect to human tumor cells, is caused by the over expression of certain membrane bound proteins relative to normal cells. These membrane bound proteins or MDR proteins include the MDR1 protein (alternatively termed P-glycoprotein), MRP and their functional analogs. The MDR proteins extrude the applied cytostatic agents (e.g. Vinca alkaloids, anthracycline derivatives and other clinically used effective anti cancer agents) by active membrane transport to the exterior of the cell. These over expressed proteins make use of the energy obtained from ATP hydrolysis, thus making practically impossible for the applied agents to produce their cytostatic effect.

Hydrophobic cell permeable ester derivatives of some fluorescent dyes are actively extruded from the cells by MDR proteins present in the cell membranes, before the ester derivatives can reach the cytosol. However, once the ester derivatives reach the cytosol, intracellular esterases cleave the esters from the fluorescent dyes, and the MDR proteins can not extrude the resulting free dye compounds [Homolya, L. et al, J. Biol. Chem., 268, 21493 (1993)]. It has been demonstrated that the commercially available compound, calcein-AM (calcein-acetoxy-methylester), generally used in cell viability assays, is—unlike free calcein— an excellent activator of the MDR dependent ATPase ($K_a \leq 1$ $\mu$mol/l). It has also been shown that calcein accumulation in the cell following calcein-AM uptake is reduced by the presence of MDR activity.

Calcein-AM is practically non fluorescent and highly lipid soluble (hydrophobic) and rapidly penetrates through the cell membrane. Intracellular esterases rapidly cleave the ester bond present in the compound, producing a highly fluorescent water soluble (hydrophilic) compound. When living cells are contacted with calcein-AM, calcein-AM molecules continuously penetrate the cells because of the established concentration gradient and cleavage products accumulate within the cell. The use of calcein-AM in cell viability assays is also based on this principle, since in damaged or dead cells entering calcein-AM molecules are not be transformed to a fluorescent product [Handbook of fluorescent probes and research chemicals, pp. 172–173, ed. Haugland, R. P., Molecular Probes Inc., Eugene, Oreg. (1992–94)].

It has been demonstrated that calcein-AM is useful for the qualitative functional analysis of the presence of multi-drug resistance in cells (Holló, Zs. et al, Biochim. Biophys. Acta 1191, 384 (1994); application Ser. No. 08/928,528 by Sarkadi et al, filed Sep. 12, 1997, hereby incorporated by reference; International PCT Publication No. WO 96/06945). If any of the over expressed proteins that exhibit MDR-type cell transport are present in the cell membrane, the cell extrudes the penetrating calcein-AM molecules via an active transport mechanism, and thus the rate of transformation of calcein-AM to fluorescent calcein (or other fluorescent calcein derivatives) and of accumulation of the fluorescent product(s) within the cells will be significantly reduced, relative to wild type cells. The resulting in vitro clinical diagnostic assay method makes possible, by applying a relatively simple and inexpensive measurement, the reliable pre-estimation of the measure of multi-drug resistance of different tumor types.

Clinicians are especially interested in learning the drug resistance profile, and the substrate specificity and drug extrusion activity of the various multi-drug resistance proteins in a given tumor sample. The demonstration of the transport activity of various multi-drug resistance proteins (e.g. MDR1, MRP1, cMOAT) in the plasma membrane requires a sensitive and reproducible in vitro multi-drug resistance assay.

The major requirements concerning current methods are the following: a) high sensitivity for the detection of relatively low levels of various MDR proteins; b) standardization, which is suitable for inter-laboratory comparison; c) functional characterization of the actual transport activity and substrate specificity of a given tumor sample; and d) straightforward evaluation of potential inhibitors of MDR transport activity.

The principles underlying the calcein assay method have permitted the formulation of highly advantageous assays that meet the above requirements. The assays of the invention are directed to quantitative measurement of both the degree of multi-drug resistance being exhibited (to what extent MDR-type transport is occurring in the sample cells) as well as the nature of the multi-drug resistance being exhibited (what type of expressed proteins are responsible and transport pathways utilized) in a single assay.

In addition, the instant assay permits the evaluation of potential mediators and effectors of multi-drug resistance, such as anti-cancer drugs, multi-drug resistance inhibitors, or environmental toxins. These screening assays are well-suited for high-throughput methods in a clinical setting.

BRIEF DESCRIPTION OF THE DRAWINGS

FIG. 4, Panel A depicts the results of an assay performed on three different human erythroid leukemia cell lines.

FIG. 4, Panel B depicts the determination of MDR activity of the same cell lines by measuring the accumulation of clacein in a flow cyclometer as shown on FIG. 2.

DETAILED DESCRIPTION OF THE DRAWINGS

Figure 1:
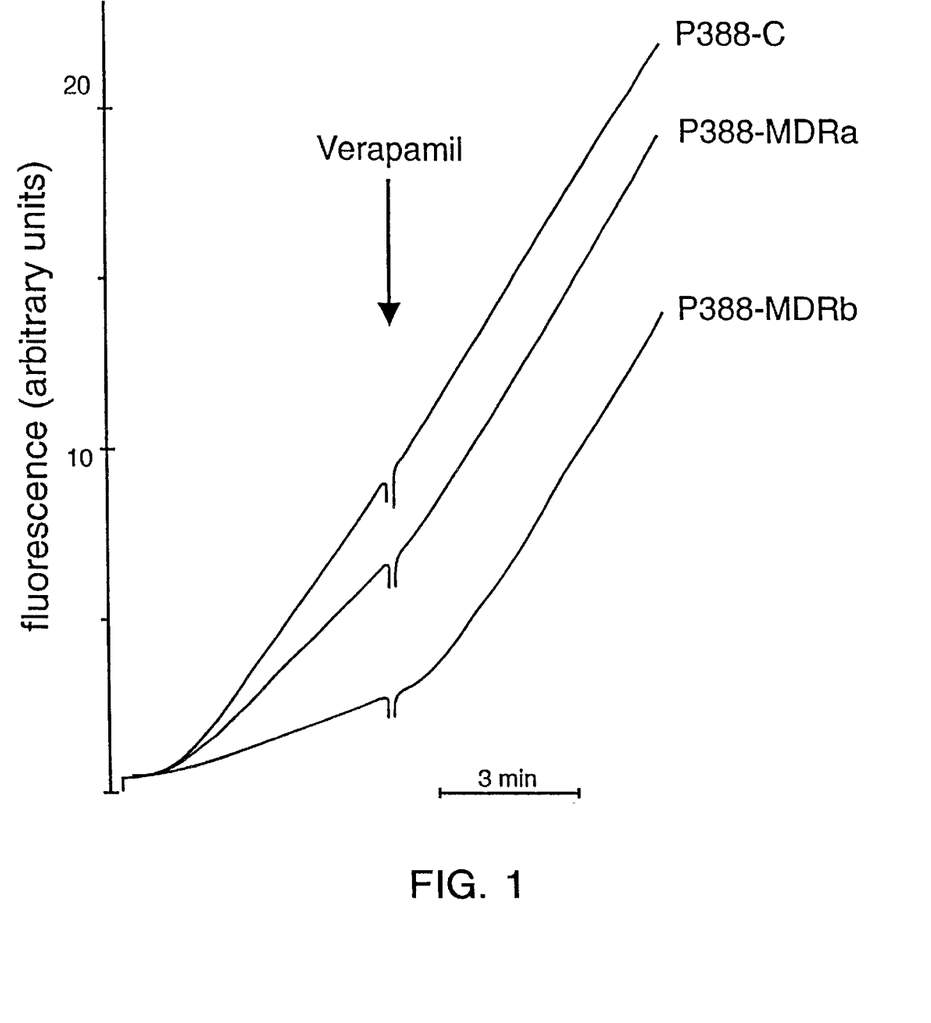
FIG. 1 is a graph showing the results of a MDR activity assay according to the invention performed on differently multi-drug resistant P-388 murine leukemia cell lines.

FIG. 1 is a graph showing the results of a MDR activity assay according to the invention performed on differently multi-drug resistant P-338 murine leukemia cell lines. In the assay shown in FIG. 1, cell suspensions of $2.5 \times 10^5$/ml concentration were incubated in 0.25 μmol/l calcein-AM at 37° C. and the rate of fluorescence increase was followed by a fluorescent spectrophotometer. Elapsed time is shown on the abscissa and fluorescence intensity in arbitrary units is shown on the ordinate. It can be seen that the steepness of the starting slope of the curves decreases with increasing multi-drug resistance of the cell lines (order of multi-drug resistance is: P388-C<P388-MDR$_a$<P388-MDR$_b$), while after addition of a transport blocking agent (verapamil) the steepness of the curves becomes similar for all the three cell lines. MDR activity factor (MAF) values (0.06<0.37<0.87) calculated on the basis of the results shown in FIG. 1 proved to be in good correlation with the measure of multi-drug resistance of the respective cell lines determined in cytotoxicity experiments (see Ex. 1).

Figure 2:
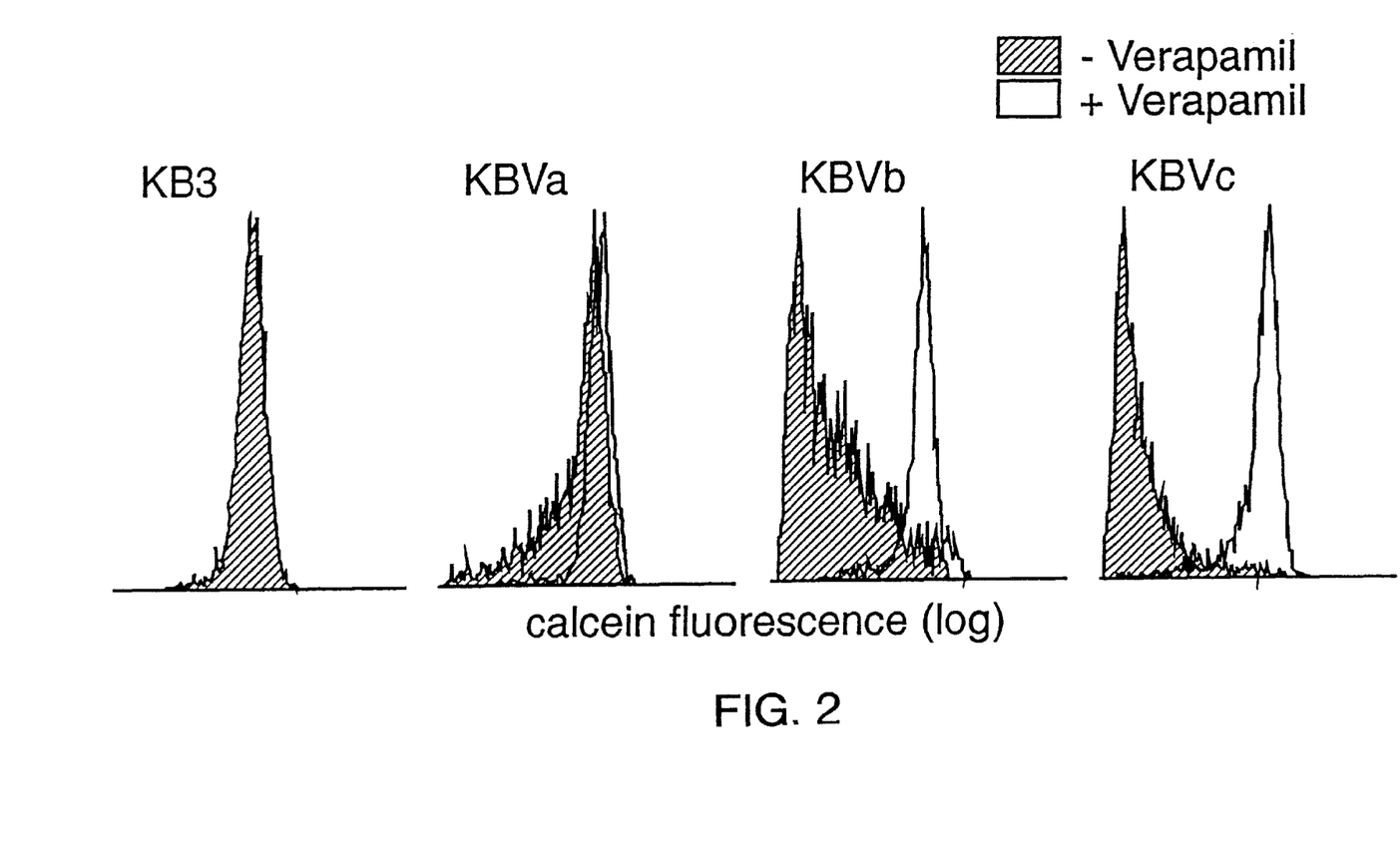
FIG. 2 shows the quantitative determination of the activity of an MDR protein measured in a flow cytometer by detecting the accumulation of calcein.

FIG. 2 shows the quantitative determination of the activity of an MDR protein measured in a flow cytometer by detecting the accumulation of calcein. In the experiments shown in FIG. 2 a drug sensitive (control, cell line KB3) and three increasingly multi-drug resistant (cell lines KB-V1$_{a-c}$) human epidermoid carcinoma cell lines were examined. Cell suspensions of $2.5 \times 10^5$/ml concentration were incubated for 10 min in 0.25 μmol/l calcein-AM at 37° C. and the fluorescence of the cells was measured in a flow cytometer. In parallel experiments, the accumulation of calcein was also measured on another parts of the same specimens that were pretreated with 100 μmol/l verapamil for 5 min (at 25° C.).

As it is well demonstrated on FIG. 2, the accumulation of calcein is decreasing with the increasing multi-drug resistance of the different cell lines (dark histograms). If MDR activity is previously blocked by incubation with verapamil, the measure of calcein accumulation reaches the control level (empty histograms). There is no detectable effect of the transport blocking agent verapamil on calcein accumulation of the control cell line (KB3). The logarithm of the intensity of green fluorescence is shown on the abscissa and cell count is shown on the ordinate. The rate of calcein accumulation and the MAF values can be calculated using the appropriate values of the shown histograms (se Ex. 1).

Figure 3:
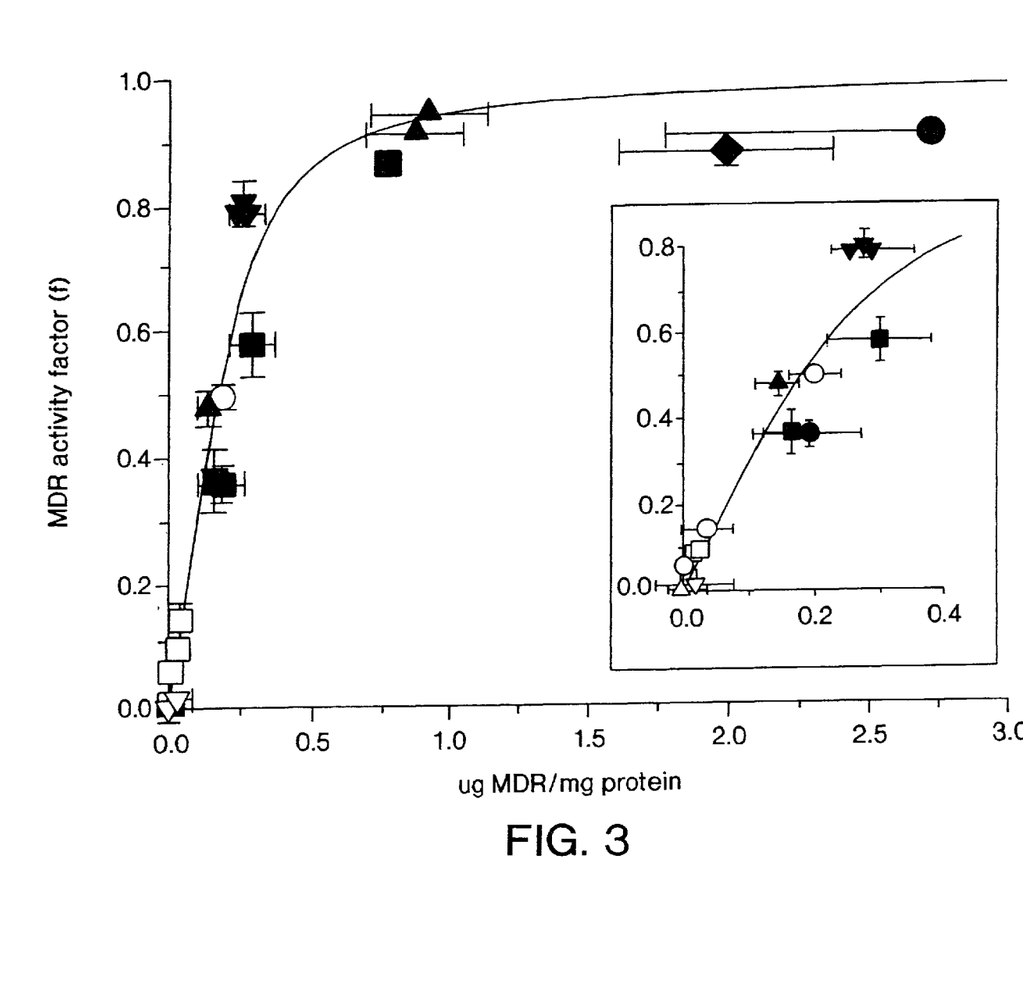
FIG. 3 is a graph showing the correlation between MAF and the concentration of the MDR protein determined by Western blot technique using the MDR-specific antibody 4077.

FIG. 3 is a graph showing the correlation between MAF and the concentration of the MDR protein determined by Western blot technique using the MDR-specific antibody 4077. All cell lines used in the demonstrated experiments are, unless specific references are given, generally available commercial cell lines. Control cell lines: murine leukemia P388-C (□), human erythroid leukemia K562C (▼), human epidermoid carcinoma KB3 (Δ), murine fibroblast NIH3T3-C (○). Differently multi-drug resistant assayed cell lines: murine leukemia P388-MDR$_{a-b}$ (■), human erythroid leukemia K562-MDR$_{a-b}$ (▽), human epidermoid carcinoma KBV1$_{a-c}$ (▲), murine erythroid leukemia F4-6 (◆) and NIH3T3-MDR, a murine fibroblast cell line stably transfected with human MDR1 (●).

As it is shown on FIG. 3, the value of MAF is monotonously increasing with the increasing concentration of expressed MDR protein. In the clinically relevant range of concentration (0–0.2 μg MDR protein/mg total protein), the value of MAF is proportional to the protein concentration (see the magnified insert on FIG. 3). It can also be seen that with decreasing concentrations of the expressed protein the sensitivity of the method of the invention is increasing (since the slope of the curve becomes steeper).

Figure 4A:
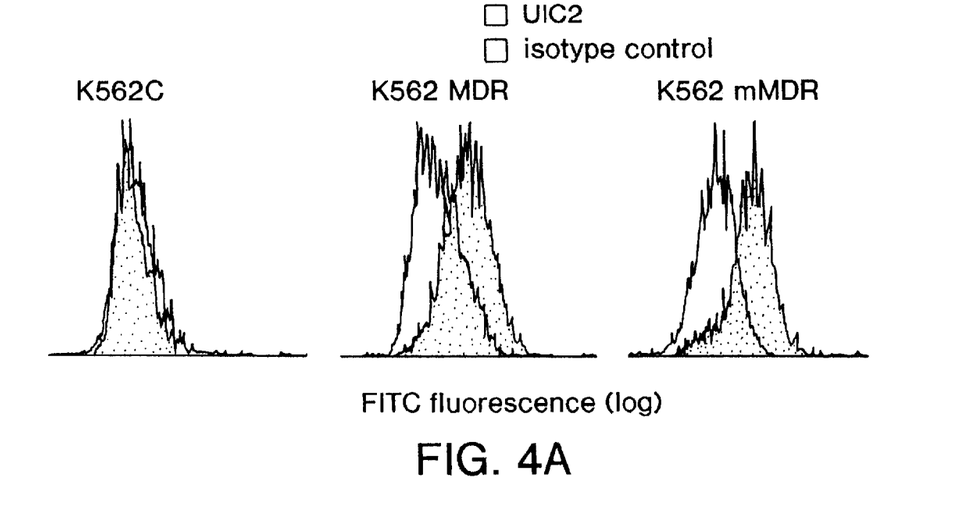

Panel A of FIG. 4 depicts the results of an assay performed on three different human erythroid leukemia cell lines: K562C (control)—a drug sensitive cell line, K562-MDR—an MDR protein expressing cell line and K562-mMDR—a cell line expressing an inactive mutant MDR protein. Concentration of the expressed MDR protein was determined by immunofluorescence applying the human MDR1 specific antibody UIC2. In the control experiment a murine IgG1 isotype antibody was used instead of the specific antibody. Signal was made visible using a FITC conjugated anti-murine IgG second antibody and the fluorescence of the cells was measured in a flow cytometer. The logarithm of the intensity of green fluorescence is shown on the abscissa and cell count is shown on the ordinate. As it can be seen on panel A, the level of MDR1 expression in cell line K562C is very low but the other two cell lines show significant MDR1 expression.

Figure 4B:
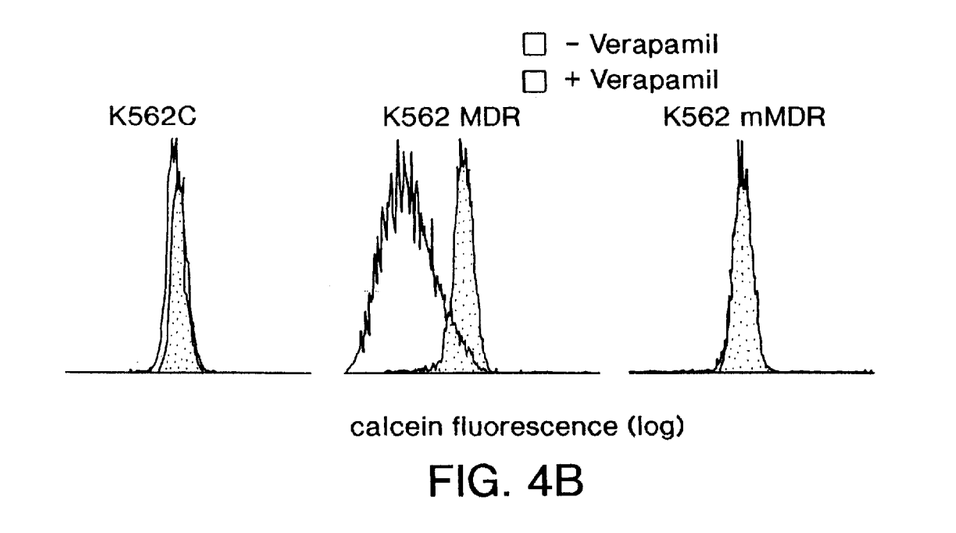

Panel B of FIG. 4 depicts the determination of MDR activity of the same cell lines by measuring the accumulation of calcein in a flow cytometer as shown on FIG. 2. Cell suspensions of $2.5 \times 10^5$/ml concentration were incubated for 10 min in 0.25 μmol/l calcein-AM at 37° C. and the fluorescence of the cells was measured in a flow cytometer (empty histograms). In parallel experiments, the accumulation of calcein was also measured on another parts of the same specimens that were pretreated with 100 μmol/l verapamil for 5 min (at 25° C., dark histograms). As it is shown on panel B of FIG. 4, the measured MDR activity is very low (f=0.11) in the case of cell line K562C expressing low levels of the MDR protein. MDR activity of cell line K562-MDR expressing high levels of a functional MDR protein is high (f=0.81), while in cell line K562-mMDR expressing an inactive mutant MDR protein, there is practically no MDR activity (f=0.006).

Figure 5:
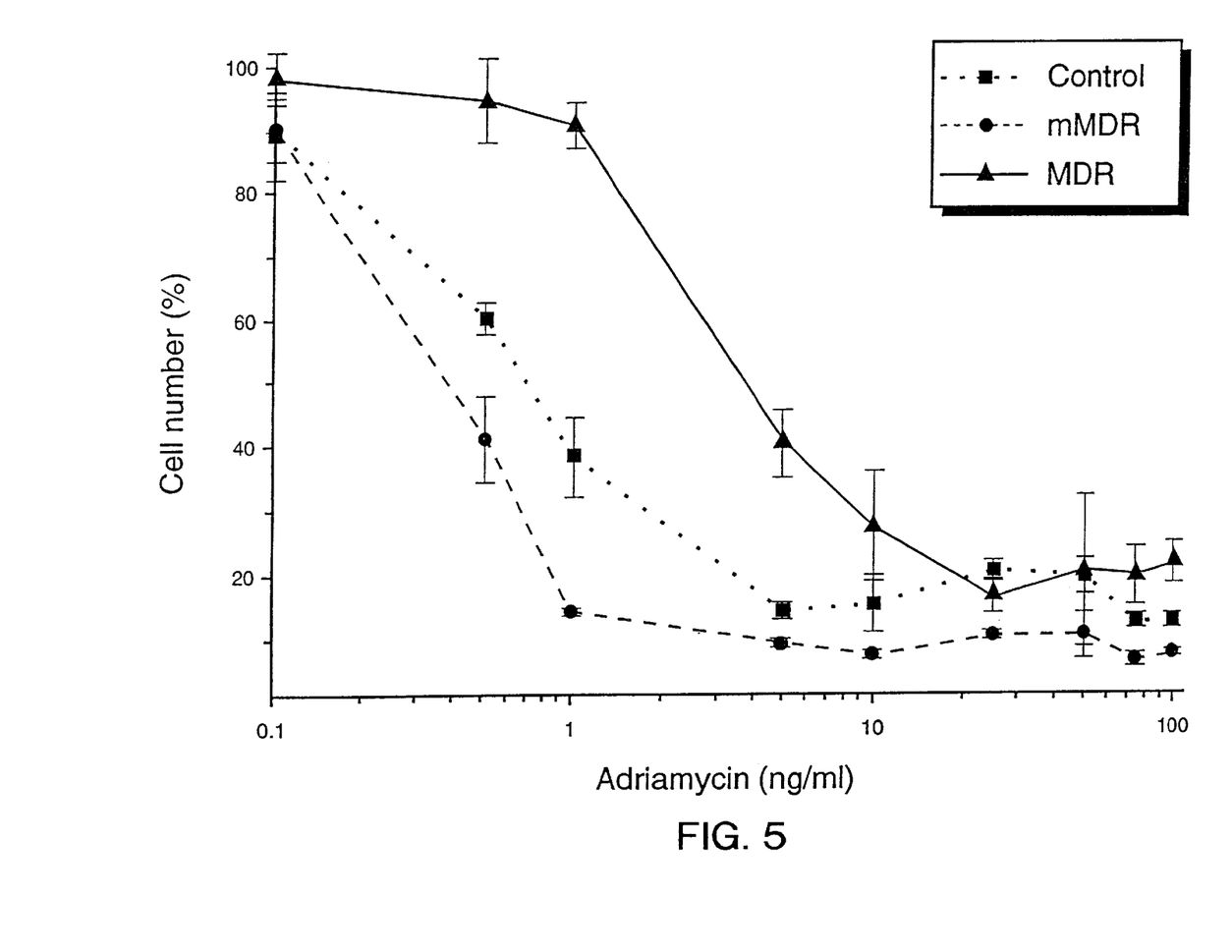
FIG. 5 depicts a cytotoxicity assay determining the drug resistance of the cell lines shown in FIG. 4.

FIG. 5 depicts a cytotoxicity assay determining the drug resistance of the cell lines shown in FIG. 4. Cells were cultured for 3 days under standard conditions in the presence of 0.1–100 ng/ml adriamycin. The number of cells in the different cell cultures is given as the percentage of the number of cells counted in the culture not treated with the drug. As it can well be seen on FIG. 5, the really expressed drug resistance is in much better accordance with the results obtained by the method of the invention based on the measurement of calcein accumulation than with those obtained by the traditional immunological measurement of MDR expression. Though cells expressing the inactive mutant MDR protein contain a high amount of said MDR protein, their multi-drug resistance is, in fact, in accordance with their real MDR activity that can be well characterized by MAF calculated on the basis of the measurement of calcein accumulation.

Figure 6:
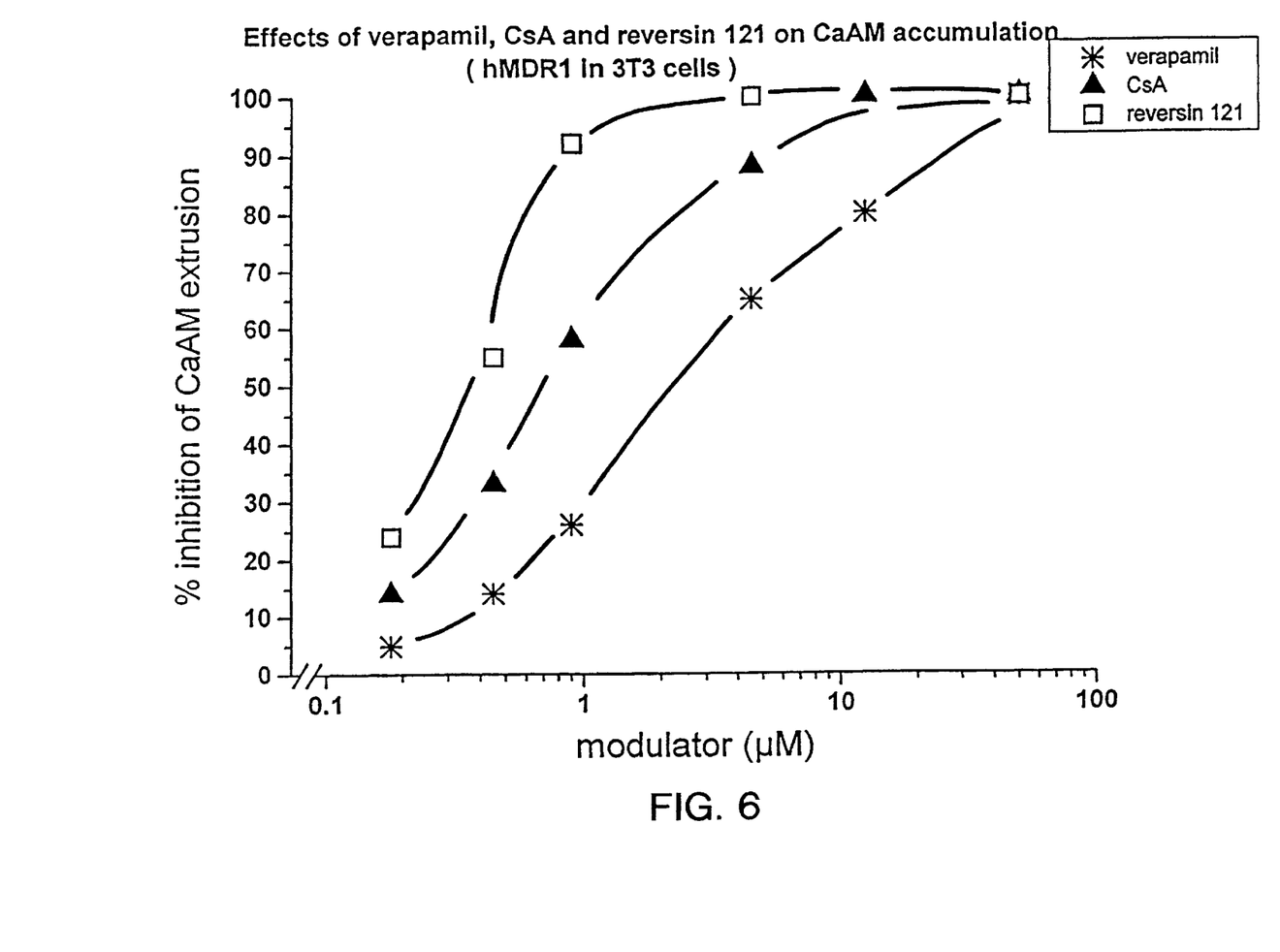
FIG. 6 shows the calculated percent inhibition of MDR1-Pgp.

FIG. 6 shows the calculated percent inhibition of MDR1-Pgp in 3T3-MDR (human MDR1-Pgp transfected mouse fibroblasts) by verapamil, CsA, and reversin 121, using the method described in Example 3.

SUMMARY OF THE INVENTION AND DESCRIPTION OF THE PREFERRED EMBODIMENTS

With respect to the present specification, we will use the foregoing technical terms in accordance with the given definition. With regard to the interpretation of the present invention, it shall be understood that the below defined terms are used in accordance with the given definitions even if said definitions are not in perfect harmony with the usual interpretation of said technical term.

A "transport protein" is a membrane bound protein that can transport a given compound through the cell membrane even against the concentration gradient by using the energy obtained through ATP hydrolysis.

"Transport protein-mediated cell efflux" is the active and effective transport of a variety of compounds to the exterior of the cell membrane, by one or more transport proteins, that are typically over expressed in the cell.

An "inhibitor of transport protein-mediated cell efflux" or "transport blocking agent" is a compound that can block the active transport of a compound of interest (e.g. calcein-AM) to the outside of the cell membrane by any mechanism of action. Transport blocking agent can be, for example, an inhibitor of the transport protein or a good substrate of same applied in excess of the amount of the compound of interest present. A "general inhibitor of transport protein-mediated cell efflux" serves to block substantially all active transport to the outside of the cell membrane, regardless of the type of transport protein that is being expressed in the sample. In contrast, a "selective inhibitor of transport protein-mediated cell efflux" serves to block only that transport that is due to a selected transport protein, or a selected transport protein-mediated efflux pathway. For example, verapamil blocks both MDR1- and MRP1-mediated cell efflux, and is a general inhibitor. In contrast, MK 571 blocks only MRP-mediated cell efflux, and is a selective inhibitor.

"MDR1 or P-glycoprotein" is a membrane bound protein of 170 kD molecular weight, functional expression of which causes multi-drug resistance of the given cell.

"MRP or Multi-drug Resistance Protein" is a 190 kDa glycoprotein belonging to a family of efflux pumps, functional expression of which confers multi-drug resistance on a given cell by mediating the ATP-dependent membrane transport of glutathione S-conjugates of chemotherapeutic drugs.

With respect to the present invention the gene product of the MDR1 gene, MRP, and their functional analogs are named "MDR proteins" without any regard to their source or to their usually accepted trivial names. In other words: the term "MDR protein" stands in the present specification for every protein causing multi-drug resistance.

A "substrate of an MDR protein" is a compound that can be extruded from the cell through an MDR mediated active transport mechanism (e.g. cytotoxic agents, cytostatic agents and other foreign extracellular compounds). "Good" substrates of an MDR protein are extruded significantly faster from the cell than those termed "not good" substrates.

The term "multi-drug resistance" denotes the occurrence of transport protein-mediated cell efflux in a cell or cells. While such cell efflux typically transports a variety of substances to the outside of the cell membrane, such transport is particularly problematic in tumor cells, where it typically interferes with therapeutic treatment of cancer due to the active transport of a wide variety cytotoxic and cytostatic agents of significantly different structure to the exterior of the cell membrane. Such tumor cells are called "multi-drug resistant" cells.

Every protein that has a function identical or similar to another protein will be termed here a "functional analog" of said second protein. Functional analogs of a protein are also structural homologues of said protein in most cases. For example, every membrane transport protein that can extrude compounds from a cell which are detrimental to any function of said cell through an active transport mechanism will be termed functional analogs of the MDR1 protein.

"Structurally homologous proteins" are those proteins that share at least one important domain or other important part of similar tertiary structure.

The term "MDR activity" denotes the activity of a protein causing multi-drug resistance, i.e. the activity of the MDR1 protein and its functional analogs.

An "easily detectable compound" is a compound the presence and/or the concentration of which can be accurately determined by eye sight or by instrumental measurement under the given conditions based on a detectable characteristic of said compound. Examples of such compounds are: colored compounds, fluorescent compounds, luminescent compounds and compounds having special catalytic or enzyme activity or compounds necessary for such activities (e.g. coenzymes).

The ATP hydrolyzing capability of an MDR protein, through which it provides energy for the active membrane transport, is termed "MDR dependent ATPase" activity herein.

"Cell permeable compound" is a usually hydrophobic compound that can enter the cell in a practically unhindered manner.

The method according to the invention comprises contacting the biological specimen—or a portion of said specimen—with a non-fluorescent and cell permeable form of calcein. This calcein compound is a good substrate for the MDR protein or proteins present in the specimen. In addition, the calcein compound is readily converted to (fluorescent) free calcein by intracellular esterase enzymes. Typically, the calcein compound of the invention is an acetoxymethyl ester or acetate ester of calcein. More typically, the calcein compound of the invention is the acetoxymethyl ester of calcein (calcein-AM).

As free calcein itself is not a substrate (or not a good substrate) of said MDR proteins, free calcein accumulates within the cells of the sample—or portion of the sample. The method of the invention further comprises the quantitative determination of the accumulation rate of calcein within the cells by the means of measuring a detectable signal (e.g. fluorescence or light absorption); and contacting the biological specimen—or another portion of said specimen—with a calcein compound as described above in the presence of a transport blocking agent; quantitatively determining the accumulation rate of calcein within the cells by the same manner; and calculating—and expressing in desired diagnostic units—the activity and/or concentration of said biologically active MDR protein present in said specimen by applying an empirically established correlation.

Calcein is a derivative of fluorescein, and exhibits bright green fluorescence. The molar fluorescence emission coefficient of free calcein is very high, and its excitation and emission parameters (excitation: 490 nm; emission: 515 nm) make it a useful label for applications in flow cytometry, conventional fluorescence detection, or even scanning laser microscopy. The free calcein molecules produced within the cells do not leak out from the cells, are not detrimental to the cells, and their fluorescent characteristics are highly independent from different influences, thus the fluorescence of calcein is practically resistant to changes in the pH or in the concentration of $Ca^{2+}$ or $Mg^{2+}$ ions and no component usually present in the cells interferes with said fluorescence.

In one embodiment of the invention, the accumulation rate of calcein in sample cells exhibiting MDR is compared to a) the accumulation rate of calcein in the sample cells in the presence of a general inhibitor of transport protein-mediated cell efflux, and b) the accumulation rate of calcein in sample cells in the presence of a selective inhibitor of transport protein-mediated cell efflux. In this method, the type of cell efflux exhibited by the sample cells may be characterized. Typically, the selective inhibitor is an inhibitor of either MDR1 -Pgp mediated cell efflux, or MRP-mediated cell efflux.

In another embodiment of the invention, the MDR assay is modified to permit the evaluation of the effect of a test substance on cells known to exhibit transport protein-mediated cell efflux. In this embodiment of the invention, four measurements are obtained: a) calcein accumulation in the absence of both transport blocking agents and the test substance, b) calcein accumulation in the presence of a general inhibitor of transport protein-mediated cell efflux, c) calcein accumulation in the presence of the test substance, and d) calcein accumulation in the presence of both a general inhibitor of transport protein-mediated cell efflux and the test substance. In this embodiment of the invention, measurements a) and b) provide calcein accumulation values corresponding to strong MDR activity, and essentially no MDR activity (negative and positive controls, respectively). Measurement c) permits the evaluation of the test substance with regards to its ability to inhibit MDR activity, while measurement d) provides a control measurement to evaluate the contribution of the test substance's effect on cellular esterase activity to the total calcein accumulation of measurement c).

The method and reagent kits according to the invention are especially useful in human clinical diagnostics for making a fast and simple estimation on the measure of the multi-drug resistance of tumors and other cancerous cells based on the measurement of their MDR activity, which is of particular help in establishing the proper chemotherapeutic treatment required.

The present methods are based on the recognition that it is possible to elaborate simple assay methods quantitatively characterizing the concentration of the biologically active MDR transport protein in cells, i.e. the maximum MDR activity of the specimen. Such method comprises the following steps: contacting tumor cells in vitro with calcein-AM; measuring the rate of accumulation of fluorescent calcein derivative(s) within the cell; and calculating an MDR activity factor (MAF) from the measured value using an internal standard by applying empirically established correlations, said MAF being a dimensionless number and being characteristic of the measure of the MDR activity of the assayed cells regardless of the type, size and origin of the assayed cells. For calculating MAF, the measure of calcein accumulation in the cells of the assayed specimen determined in the presence of a transport blocking agent is used as the internal standard. It has been demonstrated that the concentration of MDR protein in different multi-drug resistant tumor cell lines deduced from the MAF calculated according to the method of the invention is—within the clinically important concentration range (0–0.2 $\mu$g MDR protein/mg total protein)—in very good correlation with the concentration of the functional MDR protein measured by immunological methods in the same cell lines (see Ex. 1 and FIG. 1).

It is important to emphasize with respect to the clinical diagnostic applicability of the method according to the invention that MAF calculated according to the process of the invention was—in all cases examined so far—in good correlation with the drug resistance of the given cell line determined independently in cell survival studies (Ex. 1, FIG. 1).

It has also been shown that the MAF value of a tumor cell line expressing a biologically inactive mutant MDR protein causing no drug resistance is zero, indicating that the method according to the invention characterizes the MDR activity (i.e. the drug extruding potential) of the malignant tissues in a clinically relevant manner (Ex. 2).

As the method of the invention only makes use of several non-unique characteristics of calcein-AM, it will be obvious for a person with ordinary skills in the art that any similar compound can be employed in the method of the invention instead of calcein-AM as far as all its important characteristics are similar to or identical with those of calcein-AM. Such characteristics of calcein-AM that are important with respect to the method of the invention are as follows: it is cell permeable; it is a good substrate of an MDR protein; and it is transformed in the cell by generally present enzymes to an easily detectable compound that is not a substrate (or not a good substrate) of the MDR protein and accumulates within the cell (its release from the cells is very slow).

According to one aspect of the present invention, a method is provided for the quantitative in vitro determination in biological specimens of the activity and/or concentration of a transport protein causing multi-drug resistance in tumors or other cancerous cells, comprising:

a) contacting said specimen or a part of said specimen with a derivative of an easily detectable compound, said derivative being a good substrate of said transport protein and being able to enter the cells of said specimen, and within the cells of said specimen said derivative is transformed to an easily detectable compound as the consequence of the action of an enzyme(s) present within said cells, said easily detectable compound not being a substrate (or not being a good substrate) of said transport protein and accumulates within said cells;

b) determining quantitatively the rate of accumulation (F) of said easily detectable compound within said cells; and then     c) contacting said assayed specimen or another part of said assayed specimen with said derivative of said easily detectable compound in the presence of a transport blocking agent; and     d) determining quantitatively the rate of accumulation (F*) of said easily detectable compound within said cells in the same manner as previously; characterized in         (i) calculating the value of the dimensionless MAF characteristic of the measure of the activity of said transport protein present in said specimen based on the empirically established correlation MAF=(F*−F)/F*; and         (ii) optionally deducing and expressing in desired diagnostic units the concentration of the biologically active MDR protein in said specimen and/or the MDR activity of said specimen, said deduction being made from the previously calculated MAF value applying an empirically established table and/or graph and/or other empirically established mathematical correlation.

In one embodiment, the instant invention further comprises a method for evaluating the effect of a test substance on transport protein-mediated cell efflux in a sample, wherein the sample comprises cells. In this embodiment, the method comprises the steps of:

a) contacting a first portion of the sample with a calcein compound that is a cell permeable form of calcein;

b) determining a first rate of calcein accumulation within the cells of said first portion of the sample;

c) contacting a second portion of the sample with the test substance and with the calcein compound;

d) determining a second rate of calcein accumulation within the cells of said second portion of the sample;

e) contacting a third portion of the sample with a general inhibitor of transport protein-mediated cell efflux in an amount sufficient to substantially inhibit said transport protein-mediated cell efflux, and with the calcein compound;

f) determining a third rate of calcein accumulation within the cells of said third portion of the sample;

g) contacting a fourth portion of the sample with the test substance, with both the general inhibitor of transport protein-mediated cell efflux, present in an amount sufficient to substantially inhibit said transport protein-mediated cell efflux, and with the calcein compound;

h) determining a fourth rate of calcein accumulation within the cells of said fourth portion of the sample;

i) calculating the difference between the first and second rates of calcein accumulation;

j) calculating the difference between the third and fourth rates of calcein accumulation;

k) correlating said difference between the first and second rates of calcein accumulation with the interaction between the test substance and transport protein-mediated cell efflux in said sample, using said difference between the third and fourth rates of calcein accumulation to correct for inhibition of cellular esterase activity by the test compound.

In this method, the rates of calcein accumulation are determined by a fluorescence measurement of the amount of free calcein accumulating in the sample cells. Any method of quantitative fluorescence measurement may be used. In one embodiment, a fluorometer is utilized. In another embodiment, a fluorescence microscope equipped with a CCD camera is used. In a preferred embodiment, the fluorescence measurements or performed using a fluorescence microplate reader, so as to facilitate clinical screening. Where a fluorometer or microplate reader is utilized, the actual fluorescence measured is dependent on the number of cells in the sample, and so must be normalized to provide an indication of the rate of calcein accumulation per cell.

The test substance may be any substance, artificial or naturally occurring, that is suspected to either inhibit or promote transport protein-mediated cell efflux. In one embodiment, the test substance is a drug, typically an anti-cancer agent. In another embodiment, the test substance is a toxin. In yet another embodiment, the test substance is a protein kinase inhibitor, a protease inhibitor, a hydrophobic drug, or a modulator of the blood-brain or blood-testis barrier. Where the test substance is a toxin, the method of the invention is optionally used to evaluate environmental toxins for their effects on MDR in biological samples.

In this method, the transport protein-mediated cell efflux under examination is optionally mediated by any transport protein expressed in the sample cells. Typically, the transport protein-mediated cell efflux is mediated by the protein MDR1-Pgp, or by the protein MRP1, or both.

In another embodiment of the invention, the instant method further comprises a method for evaluating transport protein-mediated cell efflux in a sample, wherein the method comprises the steps of:

a) contacting a first portion of the sample with a calcein compound that is a cell permeable form of calcein;

b) determining a first rate of calcein accumulation within the cells of said first portion of the sample;

c) contacting a second portion of the sample with a general inhibitor of transport protein-mediated cell efflux and the calcein compound d) determining the second rate of calcein accumulation within the cells of said second portion of the sample;

e) contacting a third portion of the sample with a selective inhibitor of one or more transport protein-mediated cell efflux pathways and the calcein compound;

f) determining a third rate of calcein accumulation within the cells of said third portion of the sample;

g) calculating the difference in said first and second rates of calcein accumulation, and correlating said difference with the transport protein-mediated cell efflux exhibited by said sample;

h) calculating the difference in said first and third rates of calcein accumulation; and correlating said difference with the transport protein-mediated cell efflux exhibited by said sample in the presence of said selective inhibitor;

i) calculating the difference in transport protein-mediated cell efflux exhibited by said sample in the presence and in the absence of said selective inhibitor; and j) correlating said difference in transport protein-mediated cell efflux with the transport protein-mediated cell efflux pathway utilized by said sample.

In one embodiment, the selective inhibitor is an inhibitor of MDR1-Pgp-mediated cell efflux. In another embodiment, the selective inhibitor is an inhibitor of MRP1-mediated cell efflux. Inhibitors of MRP- and/or MDR1-mediated cell efflux are provided in Table 1. In a preferred embodiment, the selective inhibitor is MK 571, CCCP, 2,4-DNP, Probenecid, Sulfinpyrazone, Benzbromarone, Indomethacin, N-ethylmaleimide, or Prostaglandin A1. In a more preferred embodiment, the selective inhibitor is MK 571.

TABLE 1

| | $IC_{50}$* ($\mu M$) | |
|---|---|---|
| Inhibitor | MRP | MDR1 |
| Vinblastine | 2–5 | 2–3 |
| Tamoxifen | 3–6 | 2–5 |
| Cyclosporin A | 2–4 | 0.5–1 |
| Verapamil | 4–8 | 2–5 |
| Econazole | 3–10 | 1–3 |
| Quinine | 50–100 | 20–30 |
| Oligomycin | 1–2 | 1–2 |
| CCCP | 10–30 | >200[a] |
| 2,4-DNP | 30–50 | >200[a] |
| Probenacid | 500–800 | >2000[a] |
| Sulfinpyrazone | 300–500 | >2000[a] |
| Benzbromarone | 5–10 | >500[a,b] |
| Indomethacin | 10–20 | >800[a,b] |
| Na-cholate | 200–300 | >1000[b] |
| Bromosulfophthalein | 100–150 | >1000[b] |
| Ethacrynic acid | 20–30 | >800[b] |
| Merthiolate | 10–20 | >200[b] |
| NEM | 0.2–0.5 | >50[b] |
| NPM | 0.1–0.2 | >20[b] |
| Genistein | 150–200[b] | >1000[a,b] |
| Chlorambucil | 30–50 | >500[b] |
| Prostaglandin $A_1$ | 3–5 | >100[a] |

Drug effects on MRP were estimated form calcein accumulation measurements in S1MRP and in HL60 ADR cells, while the effects on MDR1 were deduced from similar measurements in 3T3 MDR and K562 MDR cells. In each case the values represent the range obtained in at least 3 independent experiments with each cell line.
*Inhibition of MRP- or MDR1-mediated calcein-AM extrusion by various compounds was determined by measuring the rate of increase in fluorescence of free calcein for 5 minute periods, and the $IC_{50}$ values were obtained by estimating the drug concentrations resulting in 50% of the maximum transport inhibition.
> indicates that 50% inhibition could not be achieved in the measurable concentration range, and either a solubility problem ([a]) or a strong esterase inhibition ([b]) was experienced at higher concentrations.

In another embodiment, the method further comprises the addition of an additional reagent capable of distinguishing between viable and non-viable sample cells. Typically, the additional reagent is a fluorescent cell membrane-impermeant nucleic acid stain. In order to clearly differentiate the fluorescence of the additional reagent from that of calcein, it is preferred that the fluorescence of the additional reagent is detectably distinct from that of calcein. Typically, the free calcein exhibits fluorescence in the green region of the visible spectrum, while the additional reagent exhibits fluorescence in the red region of the visible spectrum. In a preferred embodiment, the additional reagent is propidium iodide.

In this method, the amount of calcein accumulated in the sample cells is determined by a fluorescence measurement. Any method of quantitative fluorescence measurement may be used to obtain the fluorescence measurement. In one embodiment, a fluorometer is utilized. In another embodiment, a fluorescence microscope equipped with a CCD camera is used. In a preferred embodiment, the fluorescence measurements are performed using a flow cytometer. The use of flow cytometry in conjunction with the additional reagent above permits the exclusion of non-viable cells from the analysis of MDR activity, and permits evaluation of MDR on a cell-by-cell basis.

For all embodiments, the specimen or sample comprises cells. Typically, the cells are eukaryotic cells, preferably animal cells, more preferably mammalian cells. In another embodiment, the sample cells are fungal, plant, or animal cells. In a preferred embodiment, the sample cells are tumor cells, typically human tumor cells.

It is another aspect of the present invention to provide reagent kits also comprising instructions for carrying out the methods of the invention.

The reagent kits according to the invention typically comprise a calcein derivative and/or an inhibitor or a good substrate of a transport protein. Typically the inhibitor is verapamil. In another embodiment, the kit further comprises a selective inhibitor of either MDR1-Pgp or MRP, preferably MK 571. In yet another embodiment, the kit further comprises an additional reagent capable of distinguishing between viable and non-viable sample cells, preferably propidium iodide.

The examples below are given so as to illustrate the practice of this invention. They are not intended to limit or define the entire scope of this invention.

EXAMPLES

Example 1

Quantitative in vitro determination of an MDR protein by measuring calcein accumulation (by fluorescent photometry and flow cytometry) in different tumor cell lines, correlation between the level of MDR protein expression and the measured MDR activity In the experiments represented in FIG. 1, P-388 murine leukemia cell lines of different levels of multi-drug resistance were employed. In the cytotoxicity assay the adriamycin resistance of cell line P388-C (control cell line) proved to be $IC_{50}=0.5$ ng/ml, while the measured $IC_{50}$ values for P388-MDR$_a$ and P388-MDR$_b$ were 4.0 ng/ml and 9.0 ng/ml, respectively. In the experiments shown in FIG. 1 cell suspensions of $2.5 \times 10^5$/ml concentration were incubated in 0.25 µmol/l calcein-AM at 37° C. and the rate of fluorescence increase was followed by a fluorescent spectrophotometer. Elapsed time is shown on the abscissa and fluorescence intensity in arbitrary units is shown on the ordinate.

In the control cells (P388-C), there is a rapid accumulation of calcein and the rate of accumulation is not influenced by the addition of a transport blocking agent (100 µmol/l verapamil). In the multi-drug resistant cells (P388-MDR$_{a-b}$), however, the initial rate of calcein accumulation, without the addition of a transport blocking agent, is much lower but after adding a transport blocking agent this initial rate significantly increases. The method of the invention can similarly be applied in the concentration ranges of $10^5$–$2 \times 10^6$/ml cells and 0.05–1 µmol/l calcein-AM. To make the determination quantitative, it is necessary to reach a 100% inhibition of the MDR activity so when applying a competitive inhibitor of the MDR protein present in the sample as a transport blocking agent (e.g. verapamil) it should be applied in high excess to the applied easily detectable compound derivative (e.g. calcein-AM). According to the method of the invention we have determined the accumulation rate of the easily detectable compound (e.g. calcein) without (F) and with the addition of a transport blocking agent (F*) from the slopes of the steady parts of the measured curves. The MAF values calculated using the MAF=(F*−F)/F* empirical correlation were as follows:

| P388-C | 0.059, |
|---|---|
| P388-MDR$_a$ | 0.365, |
| P388-MDR$_b$ | 0.867. |

These values are in very good accordance with the drug resistance values determined in the cytotoxicity assays.

We have demonstrated in FIG. 2 the quantitative determination of the activity of an MDR protein measured in a flow cytometer by detecting the accumulation of calcein. In the experiments shown in FIG. 2 a drug sensitive (control, cell line KB3) and three increasingly multi-drug resistant (cell lines KB-V1$_{a-c}$) human epidermoid carcinoma cell lines were examined. Cell suspensions of $2.5 \times 10^5$/ml concentration were incubated for 10 min in 0.25 µmol/l calcein-AM at 37° C. and the fluorescence of the cells was measured in a flow cytometer. In parallel experiments, the accumulation of calcein was also measured on another parts of the same specimens that were pretreated with 100 µmol/l verapamil for 5 min (at 25° C.).

As it is well demonstrated in FIG. 2, the accumulation of calcein is decreasing with the increasing multi-drug resistance of the different cell lines (dark histograms). If MDR activity is previously blocked by incubation with verapamil, the measure of calcein accumulation reaches the control level (empty histograms). There is no detectable effect of the transport blocking agent verapamil on calcein accumulation of the control cell line (KB3). The logarithm of the intensity of green fluorescence is shown on the abscissa and cell count is shown on the ordinate. As all the specimens were incubated for the same time (10 min) with calcein-AM, the measure of the accumulation of calcein detected exactly after 10 minutes can be taken as the rate of calcein accumulation. Thus MAF values calculated from the fluorescence values determined after exactly 10 min of incubation without (F) and with the addition of a transport blocking agent (F*), based on the empirically established correlation MAF=(F*−F)/F* were as follows:

| KB3 | 0.02, |
|---|---|
| KB-V1$_a$ | 0.43, |
| KB-V1$_b$ | 0.74, |
| KB-V1$_c$ | 0.92. |

Instead of the absolute fluorescence values, the mean channel numbers in a logarithmic scale can also be used when calculating the MAF value. In such a case a modified empirical correlation is to be used for the calculation as follows:

$$MAF = 1 - e^{k(G-G^*)}$$

wherein G is the mean channel number measured in the absence of a transport blocking agent, G* is the mean channel number measured in the presence of a transport blocking agent and k is a constant used for the calculation of the absolute fluorescence values that is characteristic of the flow cytometer applied.

in FIG. 3 the correlation between MAF and the concentration of the MDR protein is shown. MAF values were determined for several differently multi-drug resistant cell lines by the fluorescent photometric method shown on FIG. 1 on the basis of the calcein accumulation curves.

In parallel experiments the concentration of the expressed MDR protein in the same cell lines were determined by Western blot technique applying the MDR-specific antibody 4077. For the description of the applied materials and methods see the following publications: Homolya, L. et al, J. Biol. Chem., 268, 21493 (1993) and Holló, Zs. et al, Biochim. Biophys. Acta 1191, 384 (1994). The concentration of the expressed MDR protein was determined from the measured luminescence values by comparison with a specimen of known MDR protein concentration. Control cell lines: murine leukemia P388-C (□), human erythroid leukemia K562C (▽), human epidermoid carcinoma KB3 (△), murine fibroblast NIH3T3-C (○). Differently multi-drug resistant assayed cell lines: murine leukemia P388-MDR$_{a-b}$ (■), human erythroid leukemia K562-MDR$_{a-b}$ (▼), human epidermoid carcinoma KBV1$_{a-c}$ (▲), murine erythroid leukemia F4-6 (♦) and NIH3T3-MDR, a murine fibroblast cell line stably transfected with human MDR1 (●).

As it is shown in FIG. 3, the value of MAF is monotonously increasing with the increasing concentration of expressed MDR protein. In the clinically relevant range of concentration (0–0.2 μg MDR protein/mg total protein), the value of MAF is proportional to the protein concentration (see the magnified insert on FIG. 3). Additionally, it can also be seen that with decreasing concentrations of the expressed protein the sensitivity of the method of the invention is increasing (since the slope of the curve becomes steeper).

Example 2

Quantitative in vitro determination of an expressed mutant MDR protein by using an immunological method and the quantitative determination of its MDR activity by measuring calcein accumulation In FIG. 4, we have demonstrated the results of an assay performed on three different human erythroid leukemia cell lines: K562C (control)—a drug sensitive cell line, K562-MDR—an MDR protein expressing cell line and K562-mMDR—a cell line expressing an inactive mutant MDR protein. Concentration of the expressed MDR protein was determined by immunofluorescence applying the human MDR1 specific antibody UIC2. In the control experiments a murine IgG1 isotype antibody was used instead of the specific antibody. Antibody labeling was visualized by using an FITC conjugated anti-murine IgG second antibody and the fluorescence of the cells was measured in a flow cytometer. The logarithm of the intensity of green fluorescence is shown on the abscissa and cell count is shown on the ordinate. As it can be seen on panel A, the level of MDR1 expression in cell line K562C is very low but the other two cell lines show significant MDR1 expression.

In panel B of FIG. 4, the determination of MDR activity of the same cell lines is shown by measuring the accumulation of calcein in a flow cytometer as shown on FIG. 2. Cell suspensions of 2.5×10$^5$/ml concentration were incubated for 10 min in 0.25 μmol/l calcein-AM at 37° C. and the fluorescence of the cells was measured in a flow cytometer (empty histograms). In parallel experiments, the accumulation of calcein was also measured on another parts of the same specimens that were pretreated with 100 μmol/l verapamil for 5 min (at 25° C., dark histograms). As is shown in panel B of FIG. 4, the measured MDR activity is very low (f=0.11) in the case of cell line K562C expressing low levels of the MDR protein. MDR activity of cell line K562-MDR expressing high levels of a functional MDR protein is high (f=0.81), while in cell line K562-mMDR expressing an inactive mutant MDR protein, there is practically no MDR activity (f=0.006).

In FIG. 5, we have demonstrated the results of a cytotoxicity assay determining the drug resistance of the cell lines shown in FIG. 4. Cells were cultured for 3 days under standard conditions in the presence of 0.1–100 ng/ml adriamycin. The number of cells in the different cell cultures is given as the percentage of the number of cells counted in the culture not treated with the drug.

The results of the three assay performed are summarized in Table 2:

TABLE 2

| Cell line | MDR concentration (UIC2 signal compared to the control) | MAF value | Resistance to Adriamycin (IC$_{50}$, ng/ml) |
|---|---|---|---|
| K562-C | 1.09 × | 0.11 | 0.7 |
| K562-MDR | 3.98 × | 0.81 | 3.1 |
| K562-mMDR | 4.18 × | 0.006 | 0.35 |

As can be seen from the above table, the expressed drug resistance is in much better accordance with the results obtained by the method of the invention based on the measurement of calcein accumulation than with those obtained by the traditional immunological measurement of MDR expression. Although cells expressing the inactive mutant MDR protein contain a high amount of said MDR protein, their multi-drug resistance is, in fact, low. The MAF for these cells, calculated on the basis of the measurement of calcein accumulation, provides a much better correspondence with the MDR activities of the subject cells.

From the experimental results demonstrated above and from the accompanying teachings, it should be evident for the skilled artisan that the assay methods according to the invention enable the quantitative functional in vitro clinical diagnostic determination of the activity and concentration of proteins such as MDR1 or P-glycoprotein that cause multi-drug resistance in different tumors. This is why the method of the present invention, by the in vitro determination of the MDR activity expressed in the tumor cells, makes possible better planning and execution of chemotherapeutic treatments in case of multi-drug resistant tumors reducing both the detrimental side effects and the costs of said treatments.

Example 3

Screening of potential MDR inhibitors using a fluorescence microplate reader

A 0.5 μM solution of the acetoxymethyl ester of calcein (calcein-AM) in Hanks Balanced Salt solution (HBSS) is prepared. A suspension of 10$^6$ cells known to exhibit MDR transport is prepared. An aliquot of 100 μL of the cell suspension is distributed to each well of a 96 well microplate.

1—1 μL of DMSO is added to 3 wells. 1—1 μL of Verapamil is added to wells #4–6. A serial dilution of the substance to be tested is prepared, and wells are prepared that contain both verapamil (1 μL) and 1 μL of the dilution of the substance to be tested. An aliquot of 100 μL of the calcein-AM/HBBS solution is added to each well. The samples are gently mixed by pipetting, and incubated at 37° C.

The green fluorescence of each well is determined using a fluorescence reader for tissue culture plates. The inhibition of MDR1/MRp is then calculated based on the degree of green fluorescence accumulated within the samples, as discussed above. The results for verapamil, CsA and reversin 121 in hMDR1 in 3T3 cells are shown in FIG. 6.

Example 4

Analysis of MDR transport in sample cells using flow cytometry

A 1.25 μM solution of calcein-AM in HBSS is prepared. A cell suspension is prepared containing 1–5×10$^6$ tumor cells in 8 mL of HBBS, from which 9 samples are removed, each containing 790 μL of the cell suspension, and placed in numbered MICROTUBES. To each tube is added 5 μL of 1 mg/mL solution of propidium iodide in distilled water. To tubes #1–3 are added 5—5 μL DMSO. To tubes #4–6 are added 5—5 μL of a 10 mM verapamil solution in DMSO. To tubes #7–9 are added 5—5 μL of 2 mM solution of MK571 in DMSO. All the sample tubes are mixed well be gentle pipetting, and allow to incubate for 5 minutes at 37° C.

To each tube is added 200 μL of the 1.25 μM solution of calcein-AM. Each tube is mixed by gentle pipetting, and incubated at 37° C. for exactly 10 minutes. The samples are then transferred onto ice to stop all activity, and rapidly centrifuged (1 minute, 2,000×g). The supernatant liquid in each tube is discarded, and the cells are resuspended in 0.5 mL HBBS.

The green and red fluorescence of the sample cells are measured using a flow cytometer. The tumor cells are selected in a forward scatter (FSC) versus side scatter (SSC) plot. Living (or viable) cells are selected in a red fluorescence plot (those cells showing little or no propidium iodide staining). The absolute mean/median green fluorescence values are determined for the selected populations in each sample. The average of the mean fluorescence values of the samples are calculated from the triplicate measurements:

$F_0$ from tubes #1–3

$F_{ver}$ from tubes #4–6

$F_{MK}$ from tubes #7–9

The total multi-drug resistance activity factor ($MAF_T$) is calculated according to the following equation:

$$MAF_T=100\times[(F_{ver}-F_0)/F_{ver}]$$

The degree of multi-drug resistance due to MRP expression ($MAF_{MRP}$) is calculated according to the following equation:

$$MAF_{MRP}=100\times[(F_{MK}-F_0)/F_{MK}]$$

The degree of multi-drug resistance due only to MDR1 protein expression ($MAF_{MDR}$) is then readily calculated by subtracting $MAF_{MRP}$ from $MAF_T$:

$$MAF_{MDR}=MAF_T-MAF_{MRP}$$

It is to be understood that, while the foregoing invention has been described in detail by way of illustration and example, numerous modifications, substitutions, and alterations are possible without departing from the spirit and scope of the invention as described in the following claims.

What is claimed is:

1. A method for evaluating the effect of a test substance on transport protein-mediated cell efflux in a sample comprising cells, said method comprising the steps of:

a) contacting a first portion of the sample with a calcein compound that is a cell permeable form of calcein;

b) determining a first rate of calcein accumulation within the cells of said first portion of the sample;

c) contacting a second portion of the sample with the test substance and with the calcein compound;

d) determining a second rate of calcein accumulation within the cells of said second portion of the sample;

e) contacting a third portion of the sample with a general inhibitor of transport protein-mediated cell efflux in an amount sufficient to substantially inhibit said transport protein-mediated cell efflux, and with the calcein compound;

f) determining a third rate of calcein accumulation within the cells of said third portion of the sample;

g) contacting a fourth portion of the sample with the test substance, with the general inhibitor of transport protein-mediated cell efflux in an amount sufficient to substantially inhibit said transport protein-mediated cell efflux, and with the calcein compound;

h) determining a fourth rate of calcein accumulation within the cells of said fourth portion of the sample;

i) calculating the difference between the first and second rates of calcein accumulation;

j) calculating the difference between the third and fourth rates of calcein accumulation;

k) correlating said difference between the first and second rates of calcein accumulation with the interaction between the test substance and transport protein-mediated cell efflux in said sample, using said difference between the third and fourth rates of calcein accumulation to correct for inhibition of cellular esterase activity by the test compound.

2. A method, as claimed in claim 1, wherein said determining steps are performed utilizing a fluorescence microplate reader.

3. A method, as claimed in claim 1, wherein said sample comprises eukaryotic cells.

4. A method, as claimed in claim 1, wherein said sample comprises mammalian cells.

5. A method, as claimed in claim 1, wherein the transport protein-mediated cell efflux is mediated by MDR1-Pgp, or MRP1, or both.

6. A method, as claimed in claim 1, wherein the test substance is a drug.

7. A method, as claimed in claim 5, wherein the test substance is an anti-cancer agent.

8. A method, as claimed in claim 1, wherein said test substance is selected from the group consisting of a protein kinase inhibitor, a protease inhibitor, a hydrophobic drug, a modulator of the blood-brain barrier and a modulator of blood-testis barrier.

9. A method, as claimed in claim 1, wherein said test substance is a toxin.

10. A method, as claimed in claim 1, wherein said determining steps are performed utilizing a fluorescence microplate reader;

said sample comprises eukaryotic cells;

said transport protein-mediated cell efflux is mediated by MDR1-Pgp, or MRP1, or both; and said calcein compound is the acetoxymethyl ester of calcein.

* * * * *